United States Patent
Bian et al.

(10) Patent No.: US 10,457,910 B2
(45) Date of Patent: Oct. 29, 2019

(54) METHOD FOR DEEP DEHYDRATION AND DESICCATION OF CYANOBACTERIA

(71) Applicant: JIANGSU PROVINCIAL ACADEMY OF ENVIRONMENTAL SCIENCE, Nanjing, Jiangsu (CN)

(72) Inventors: Bo Bian, Jiangsu (CN); Binbin Fang, Jiangsu (CN); Lingjun Zhou, Jiangsu (CN); Haisuo Wu, Jiangsu (CN); Qin Zhang, Jiangsu (CN); Weili Jiang, Jiangsu (CN); Wei Cheng, Jiangsu (CN); Yamin Fan, Jiangsu (CN)

(73) Assignee: JIANGSU PROVINCIAL ACADEMY OF ENVIRONMENTAL SCIENCE, Nanjing, Jiangsu (CN)

( * ) Notice: Subject to any disclaimer, the term of this patent is extended or adjusted under 35 U.S.C. 154(b) by 649 days.

(21) Appl. No.: 15/138,356

(22) Filed: Apr. 26, 2016

(65) Prior Publication Data
US 2017/0211038 A1    Jul. 27, 2017

(30) Foreign Application Priority Data
Jan. 26, 2016    (CN) .......................... 2016 1 0051759

(51) Int. Cl.
| C12N 1/20 | (2006.01) |
| C12N 1/00 | (2006.01) |
| C12N 1/02 | (2006.01) |
| C12N 1/12 | (2006.01) |

(52) U.S. Cl.
CPC .............. *C12N 1/20* (2013.01); *C12N 1/005* (2013.01); *C12N 1/02* (2013.01); *C12N 1/12* (2013.01)

(58) Field of Classification Search
None
See application file for complete search history.

(56) References Cited

U.S. PATENT DOCUMENTS 5,874,701 A * 2/1999 Watanabe ................ A61L 9/20
                                                204/157.15

FOREIGN PATENT DOCUMENTS

| CN | 104370431 A | * | 2/2015 | |
| CN | 105039160 A | * | 11/2015 | |
| CN | 204848520 U | * | 12/2015 | |
| WO | WO-2010140037 A1 | * | 12/2010 | ............. C12N 1/005 |

OTHER PUBLICATIONS

Naes ("Effect of Photon Fluence Rate and Specific Growth Rate on Geosmin Production of the Cyanobacterium Oscillatoria brevis (Kutz.) Gom.", Applied and Environmental Microbiology, 1985, 1538-1540) (Year: 1985).*

* cited by examiner

Primary Examiner — Robert J Yamasaki
Assistant Examiner — Charles Zoltan Constantine
(74) Attorney, Agent, or Firm — Rankin, Hill & Clark LLP

(57) ABSTRACT

A method for deep dehydration and desiccation of cyanobacteria includes steps of flocculation conditioning, high pressure diaphragm plate-frame pressure filtration, quartz glass box-type desiccation and negative pressure paddle drying.

6 Claims, 1 Drawing Sheet

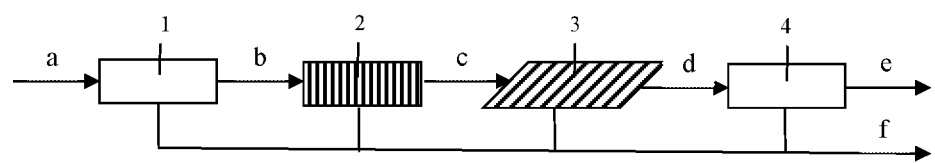

METHOD FOR DEEP DEHYDRATION AND DESICCATION OF CYANOBACTERIA

FIELD OF THE INVENTION

The present invention belongs to the field of cyanobacteria treatment, specifically the present invention relates to a method for deep dehydration and desiccation of cyanobacteria.

BACKGROUND OF THE INVENTION

Over the years, with development of agriculture and industry, increase in population, and arbitrary use of chemical fertilizer and pesticide etc, eutrophication degree of many water bodies are deepened, this may surely result in frequent occurrence of cyanobacteria bloom event.

Cyanobacteria has abundant potential resources, it is rich in a large amount of amino-acids, unsaturated fatty acids, saccharides and minerals etc, and it can be used in producing numerous biomasses and energy materials. However, prior to extraction of useful substances in the cyanobacteria, it is undoubtedly required to conduct dehydration to it. This not only resolves the problem of damage to the environment due to massive accumulation of the cyanobacteria, but also makes full use of potential of the cyanobacteria.

So far, there are many researches on the method for dehydration and drying of the cyanobacteria salvaged from water. And another research method is adding an oxidizing agent into the cyanobacteria, then conducting a microwave irradiation, finally conducting a pressure filtration dehydration to realize detoxification and dehydration, but this method adopts treatment by microwave etc, thus the energy consumption is large and the cost is high; another research method is conducting a concentration treatment to the salvaged cyanobacteria then mixing with a carrier, and laying and spreading the cyanobacteria on a screen for natural drying, but it has shortcomings of covering a large area and spending a long time for drying; moreover, there is also a method of conducting a mechanical pressure filtration to the cyanobacteria after thermal conditioning then conducting a drying for purpose of deep dehydration, however in this method a large amount of energy is consumed and the dehydration effect is not quite ideal. Therefore, researches on new efficient and low energy consumption technique for deep dehydration and desiccation of the cyanobacteria are important for subsequent resource utilization of the cyanobacteria.

SUMMARY OF THE INVENTION

The technical problem to be resolved by the present invention is providing a method for deep dehydration and desiccation of cyanobacteria, in order to resolve the problems of high cost, long time and unsatisfactory effect existing in the prior art.

To resolve the above-described technical problems, the present invention adopts a technical solution as follows:

A first technical solution realizing the present invention is as follows:

A method for deep dehydration and desiccation of cyanobacteria, it comprises the steps as follow:

(1) flocculation conditioning: a flocculant is added into a cyanobacteria slurry discharged from an algae-water separation station and a conditioning is conducted for 10-20 min;

(2) high pressure diaphragm plate-frame pressure filtration: the cyanobacteria slurry after the flocculation conditioning is pumped into a high pressure diaphragm plate-frame for pressure filtration, the water content of the cyanobacteria slurry after the pressure filtration is below 80 wt %;

(3) quartz glass box-type desiccation: the cyanobacteria slurry after the pressure filtration is desiccated in a quartz glass box.

In step (1), said flocculant is anionic polyacrylamide (PAM); wherein, mass of the flocculant is 1-5‰ of dry matter mass of the cyanobacteria slurry, said dry matter of the cyanobacteria slurry refers to mass of the remainder after the moisture being deducted from the cyanobacteria slurry.

In step (2), a feeding pressure at which the cyanobacteria slurry after the flocculation conditioning being pumped into the high pressure diaphragm plate-frame is 0.6-1.2 MPa; pressure of the pressure filtration in the high pressure diaphragm plate-frame is 1.6-2.5 MPa, and duration of the pressure filtration is 120-180 min.

In step (3), a top surface of said quartz glass box is a quartz glass with high transparency, the material of periphery and underside of the box is corrosion-resistant stainless steel;

wherein, a polymer hydrophobic membrane is stuck at an inner surface of the quartz glass with high transparency, and the contact angles of two surfaces of the polymer hydrophobic membrane are both greater than 75°;

wherein, light transmittance of the quartz glass with high transparency is greater than 90%, average light reflectivity is below 4%, and minimum of the light reflectivity is less than 0.5%.

In step (3), duration of the desiccation is preferably 1-3 days.

A preferable technical solution is: step (4) i.e. a negative pressure paddle drying is conducted after the desiccation of step (3) being complete, that is the desiccated cyanobacteria slurry obtained in step (3) is dried in a paddle dryer for 60-180 min. Step (1) to step (4) constitutes a second technical solution realizing the present invention. Wherein, said paddle dryer conducts indirect drying for the cyanobacteria slurry by using steam as the heat source, pressure of the steam is 0.2-0.8 MPa; the cyanobacteria slurry lies in a drying chamber of the paddle dryer, a negative pressure of 0.02-0.05 MPa is maintained in the drying chamber.

A third technical solution realizing the present invention is as follows:

A method for deep dehydration and desiccation of cyanobacteria, it comprises the steps as follows:

(□) flocculation conditioning: a flocculant is added into the cyanobacteria slurry discharged from an algae-water separation station and conditioning is conducted for 10-20 min;

(□) high pressure diaphragm plate-frame pressure filtration: the cyanobacteria slurry after the flocculation conditioning is pumped into the high pressure diaphragm plate-frame for pressure filtration, and water content of the cyanobacteria slurry after pressure filtration is below 80 wt %;

(□) negative pressure paddle drying: the cyanobacteria slurry after the pressure filtration is dried in a paddle dryer for 1-8 hours, obtaining a cyanobacteria slurry with a water content below 10 wt %.

In step (□), said flocculant is anionic polyacrylamide; wherein, mass of the flocculant is 1-5‰ of dry matter mass of the cyanobacteria slurry.

In step (□), feeding pressure at which the cyanobacteria slurry after the flocculation conditioning being pumped into the high pressure diaphragm plate-frame is 0.6-1.2 MPa;

pressure of the pressure filtration in the high pressure diaphragm plate-frame is 1.6-2.5 MPa, duration of the pressure filtration is 120-180 min.

In step (□), said paddle dryer conducts an indirect drying to the cyanobacteria slurry by using steam as the heat source, and pressure of the steam is 0.2-0.8 MPa; wherein, the cyanobacteria slurry lies in the drying chamber of the paddle dryer, a negative pressure of 0.02-0.05 MPa is maintained in the drying chamber.

The water content of the cyanobacteria slurries after being treated by three above-described methods are all below 10 wt %.

After two steps of the flocculation conditioning and the high pressure diaphragm plate-frame pressure filtration, if the water content of the cyanobacteria slurry is reduced to 10 wt % only by the quartz glass box-type desiccation, duration of the desiccation is preferably 1-3 days; if the water content of the cyanobacteria slurry is reduced to 10 wt % by first desiccation with the quartz glass box-type then by the drying with the paddle dryer, duration of the desiccation is preferably 12-32 hours, and duration of the drying is preferably 60-180 min; if the water content of the cyanobacteria slurry is reduced to 10 wt % only by drying with the paddle dryer, duration of the drying is preferably 1-8 hours.

Beneficial effects: compared with the prior art, the process of the present invention has the advantages as follows:

1. After adding the flocculant into the cyanobacteria slurry for conditioning, through pressure filtration of the high pressure diaphragm plate-frame, water content of the cyanobacteria slurry can be greatly reduced, this saves a large amount of energy consumption for the subsequent desiccation procedure.

2. By adopting the box-type desiccation, the natural resources are fully used, and the cost is low, the efficiency is high, the water content of the cyanobacteria slurry is further decreased, and the cost of the desiccation is saved greatly.

3. Being dried with a dryer, sensible heat in the cyanobacteria slurry is heated, and the process flow of the drying can be shortened greatly, and energy consumption of the desiccation procedure is reduced greatly.

4. The process flow of the present invention is simple, and the box-type desiccation and the drier desiccation can be conducted separately or in combination, the operation is convenient, and the operating cost is low.

BRIEF DESCRIPTION OF THE DRAWINGS

FIG. 1 is a schematic flowchart of Example 3; wherein, 1 is a conditioning tank of the cyanobacteria slurry, 2 is a high pressure diaphragm plate-frame, 3 is a quartz glass box, 4 is a paddle dryer, a is a cyanobacteria slurry discharged from the algae-water separation station, b is a cyanobacteria slurry obtained after the flocculation conditioning, c is a filter cake of the cyanobacteria slurry obtained after the pressure filtration, d is a cyanobacteria slurry obtained after the desiccation, e is a cyanobacteria dry powder after drying, and f is tail waters produced in each stage.

DESCRIPTION OF THE EMBODIMENTS

From the following examples, the present invention can be better understood. However, as one skilled in the art can easily understand, the content described in the examples is merely used to illustrate the present invention, and it should not and will not restrict the present invention described in detail in the claims.

Example 1

A cyanobacteria slurry with a water content of 96 wt % was pumped into the cyanobacteria slurry conditioning tank 1 by the algae-water separation station, and anionic polyacrylamide whose mass being 1‰ of the cyanobacteria slurry was added, then a flocculation conditioning was conducted.

The cyanobacteria slurry after the flocculation conditioning was pumped into a high pressure diaphragm plate-frame 2 by a high pressure screw pump for pressure filtration; wherein, the feeding pressure was 1.0 MPa, the pressure for a second pressing in the high pressure diaphragm plate-frame was 2.0 MPa, duration of the pressing was 180 min, and the water content of the filter cake of the cyanobacteria slurry obtained after the pressure filtration was 72 wt %.

The filter cake of the cyanobacteria slurry obtained after the pressure filtration was desiccated in the quartz glass box 3 for 3 days. The top surface of the quartz glass box was a quartz glass with high transparency, the material of periphery and underside of the box was corrosion-resistant stainless steel, and a polymer hydrophobic membrane was stuck at the inner surface of the quartz glass with high transparency. Wherein, the light transmittance of the quartz glass with high transparency was 93%, the average light reflectivity was below 4%, the minimum of the light reflectivity was less than 0.5%; and the contact angles of the inner and outer surfaces of the polymer hydrophobic membrane were respectively greater than 78° and 82°. The cyanobacteria slurry after the desiccation became a cyanobacteria dry powder with a water content of 9.3 wt %.

Example 2

The cyanobacteria slurry with a water content of 96 wt % was pumped into the cyanobacteria slurry conditioning tank 1 by the algae-water separation station, and anionic polyacrylamide whose mass being 1‰ of the mass of the cyanobacteria slurry was added, then a flocculation conditioning was conducted.

The cyanobacteria slurry after the flocculation conditioning was pumped into the high pressure diaphragm plate-frame 2 by the high pressure screw pump for pressure filtration; wherein, the feeding pressure was 1.0 MPa, the pressure of the second pressing in the high pressure diaphragm plate-frame was 2.0 MPa, duration of the pressing was 180 min, and the water content of the filter cake of the cyanobacteria slurry obtained after the pressure filtration was 70 wt %.

The filter cake of the cyanobacteria slurry obtained after the pressure filtration was dried in the paddle dryer for 3.5 hours. The paddle dryer conducted an indirect drying to the cyanobacteria slurry by using steam as the heat source, the pressure of the steam was 0.6 MPa. The cyanobacteria slurry lied in the drying chamber of the paddle dryer, and a negative pressure of 0.03 MPa was maintained in the drying chamber. The cyanobacteria slurry after drying became a cyanobacteria dry powder with a water content of 9 wt %.

Example 3

As shown in FIG. 1, the cyanobacteria slurry a with a water content of 96 wt % was pumped into the cyanobacteria slurry conditioning tank 1 by the algae-water separation station, and anionic polyacrylamide whose mass being 1‰ of the cyanobacteria slurry was added, then a flocculation conditioning was conducted.

The cyanobacteria slurry b after the flocculation conditioning was pumped into the high pressure diaphragm plate-frame 2 by the high pressure screw pump for pressure filtration; wherein, the feeding pressure was 1.0 MPa, the pressure of the second pressing in the high pressure diaphragm plate-frame was 2.0 MPa, duration of the pressing was 180 min, and the water content of the filter cake of the cyanobacteria slurry c after the pressure filtration was 72 wt %.

The filter cake of the cyanobacteria slurry c obtained after the pressure filtration was desiccated in the quartz glass box 3 for 24 hours. The top surface of the quartz glass box was quartz glass with high transparency, the material of periphery and underside of the box was corrosion-resistant stainless steel, a polymer hydrophobic membrane was stuck at the inner surface of the quartz glass with high transparency. Wherein, the light transmittance of the quartz glass with high transparency was 93%, the average light reflectivity was below 4%, minimum of the light reflectivity was less than 0.5%; the contact angles of the inner and outer surfaces of the polymer hydrophobic membrane were respectively greater than 78° and 82°. The water content of the cyanobacteria slurry obtained after the desiccation was 38 wt %.

The cyanobacteria slurry d obtained after the desiccation was dried in the paddle dryer for 120 min. The paddle dryer conducted an indirect drying to the cyanobacteria slurry by using steam as the heat source, the pressure of the steam was 0.6 MPa. The cyanobacteria slurry lied in the drying chamber of the paddle dryer, and a negative pressure of 0.04 MPa was maintained in the drying chamber. After drying, the cyanobacteria slurry became a cyanobacteria dry powder with a water content of 8 wt %.

The invention claimed is:

1. A method for deep dehydration and desiccation of cyanobacteria, comprising:
   (1) adding a flocculant into a cyanobacteria slurry discharged from an algae-water separation station for conditioning;
   (2) pumping the cyanobacteria slurry after the flocculation conditioning into a high pressure diaphragm plate-frame for pressure filtration;
   (3) desiccating the cyanobacteria slurry in a quartz glass box after the pressure filtration;
   wherein a top surface of said quartz glass box is a quartz glass with high transparency, and material of a periphery and an underside of the box is corrosion-resistant stainless steel,
   wherein a polymer hydrophobic membrane is positioned at an inner surface of the quartz glass with high transparency, and contact angles on two surfaces of the polymer hydrophobic membrane are both greater than 75°, and
   wherein light transmittance of the quartz glass with high transparency is greater than 90%, average light reflectivity is below 4%, and minimum of the light reflectivity is less than 0.5%.

2. The method for deep dehydration and desiccation of cyanobacteria according to claim 1, wherein said flocculant is anionic polyacrylamide; wherein, the mass of the flocculant is 1-5‰ of the dry matter mass of the cyanobacteria slurry.

3. The method for deep dehydration and desiccation of cyanobacteria according to claim 1, wherein a feeding pressure at which the cyanobacteria slurry after the flocculation conditioning being pumped into the high pressure diaphragm plate-frame is 0.6-1.2 MPa; a pressure of the pressure filtration in the high pressure diaphragm plate-frame is 1.6-2.5 MPa, and a duration of the pressure filtration is 120-180 min.

4. The method for deep dehydration and desiccation of cyanobacteria according to claim 1, wherein a duration of the desiccation is 1-3 days.

5. The method for deep dehydration and desiccation of cyanobacteria according to claim 1, further comprising conducting negative pressure paddle drying after the duration of the desiccation is 12-32 hours in step (3),
   wherein the dried cyanobacteria slurry obtained in step (3) is dried in a paddle dryer for 60-180 min;
   wherein, said paddle dryer conducts an indirect drying to the cyanobacteria slurry by using steam as heat source, pressure of the steam is 0.2-0.8 MPa; the cyanobacteria slurry lies in a drying chamber of the paddle dryer, and a negative pressure of 0.02-0.05 MPa is maintained in the drying chamber.

6. A method for deep dehydration and desiccation of cyanobacteria, comprising:
   (1) adding a flocculant into a cyanobacteria slurry discharged from an algae-water separation station for conditioning;
   (2) pumping the cyanobacteria slurry after the flocculation conditioning into a high pressure diaphragm plate-frame for pressure filtration;
   (3) desiccating the cyanobacteria slurry for 12-32 hours in a quartz glass box after the pressure filtration;
   (4) conducting negative pressure paddle drying after the desiccating in step (3); wherein the dried cyanobacteria slurry obtained in step (3) is dried in a paddle dryer for 60-180 min; wherein said paddle dryer conducts an indirect drying to the cyanobacteria slurry by using steam as heat source; wherein pressure of the steam is 0.2-0.8 MPa; wherein the cyanobacteria slurry lies in a drying chamber of the paddle dryer; and wherein a negative pressure of 0.02-0.05 MPa is maintained in the drying chamber.

\* \* \* \* \*